(12) United States Patent
Wysoski et al.

(10) Patent No.: US 11,298,074 B2
(45) Date of Patent: Apr. 12, 2022

(54) FLOW-BASED SLEEP STAGE DETERMINATION

(71) Applicant: Fisher & Paykel Healthcare Limited, Auckland (NZ)

(72) Inventors: Simei Gomes Wysoski, Auckland (NZ); David Robin Whiting, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 884 days.

(21) Appl. No.: 15/373,344

(22) Filed: Dec. 8, 2016

(65) Prior Publication Data

US 2017/0196500 A1 Jul. 13, 2017

Related U.S. Application Data

(60) Provisional application No. 62/264,787, filed on Dec. 8, 2015.

(51) Int. Cl.
*A61B 5/00* (2006.01)
*A61B 5/087* (2006.01)
*A61M 16/00* (2006.01)
*A61M 16/16* (2006.01)

(52) U.S. Cl.
CPC ............ *A61B 5/4812* (2013.01); *A61B 5/087* (2013.01); *A61B 5/4809* (2013.01); *A61B 5/7225* (2013.01); *A61B 5/7239* (2013.01); *A61B 5/7278* (2013.01); *A61B 5/742* (2013.01); *A61B 5/7475* (2013.01); *A61M 16/024* (2017.08); *A61M 16/16* (2013.01); *A61M 2205/502* (2013.01); *A61M 2230/40* (2013.01)

(58) Field of Classification Search
CPC ..... A61B 5/4818; A61B 5/087; A61B 5/0816; A61B 5/4812; A61B 5/4809; A61B 5/4815; A61M 2230/40
See application file for complete search history.

(56) References Cited

U.S. PATENT DOCUMENTS

| | | | |
|---|---|---|---|
| 4,655,213 A | 4/1987 | Rapoport et al. |
| 5,065,756 A | 11/1991 | Rapoport |
| 5,101,831 A | 4/1992 | Koyama et al. |
| 5,239,995 A | 8/1993 | Estes et al. |
| 5,245,995 A | 9/1993 | Sullivan et al. |
| 5,299,118 A | 3/1994 | Martens et al. |
| 5,309,921 A | 5/1994 | Kisner et al. |
| 5,335,654 A | 8/1994 | Rapoport |
| 5,433,193 A | 7/1995 | Sanders et al. |
| 5,485,851 A | 1/1996 | Erickson |

(Continued)

FOREIGN PATENT DOCUMENTS

| | | |
|---|---|---|
| EP | 0651971 | 5/1995 |
| EP | 1371384 | 12/2003 |

(Continued)

*Primary Examiner* — Christian Jang
*Assistant Examiner* — Karen E Toth
(74) *Attorney, Agent, or Firm* — Knobbe, Martens, Olson & Bear, LLP

(57) ABSTRACT

A method and system of determining a sleep stage of a user involves receiving a respiratory flow signal of a user, obtaining at least one respiratory feature from at least part of the respiratory flow signal, and determining a sleep stage from the at least one respiratory feature.

20 Claims, 12 Drawing Sheets

(56) References Cited

U.S. PATENT DOCUMENTS

| | | |
|---|---|---|
| 5,490,502 A | 2/1996 | Rapoport et al. |
| 5,492,113 A | 2/1996 | Estes et al. |
| 5,522,382 A | 6/1996 | Sullivan et al. |
| RE35,295 E | 7/1996 | Estes et al. |
| 5,535,739 A | 7/1996 | Rapoport et al. |
| 5,546,933 A | 8/1996 | Rapoport et al. |
| 5,551,418 A | 9/1996 | Estes et al. |
| 5,551,419 A | 9/1996 | Froehlich et al. |
| RE35,339 E | 10/1996 | Rapoport |
| 5,593,713 A | 1/1997 | De La Luz-Martinez et al. |
| 5,645,053 A | 7/1997 | Remmers et al. |
| 5,657,752 A | 8/1997 | Landis et al. |
| 5,732,696 A | 3/1998 | Rapoport et al. |
| 5,740,795 A | 4/1998 | Brydon |
| 5,800,360 A | 9/1998 | Kisner et al. |
| 5,803,066 A | 9/1998 | Rapoport et al. |
| 5,823,187 A | 10/1998 | Estes |
| 5,901,704 A | 5/1999 | Estes et al. |
| 5,902,250 A | 5/1999 | Verrier et al. |
| 5,904,141 A | 5/1999 | Estes et al. |
| 5,970,975 A | 10/1999 | Estes et al. |
| 6,015,388 A | 1/2000 | Sackner et al. |
| 6,083,173 A | 7/2000 | Grant et al. |
| 6,105,575 A | 8/2000 | Estes et al. |
| 6,135,106 A | 10/2000 | Dirks et al. |
| 6,142,952 A | 11/2000 | Behbehani et al. |
| 6,165,133 A | 12/2000 | Rapoport et al. |
| 6,171,258 B1 | 1/2001 | Karakasoglu et al. |
| 6,190,328 B1 | 2/2001 | Ruton et al. |
| 6,192,886 B1 | 2/2001 | Ruton et al. |
| 6,286,508 B1 | 9/2001 | Remmers et al. |
| 6,299,581 B1 | 10/2001 | Rapoport et al. |
| 6,349,724 B1 | 2/2002 | Burton et al. |
| 6,360,741 B2 | 3/2002 | Truschel |
| 6,363,933 B1 | 4/2002 | Berthon-Jones |
| 6,367,474 B1 | 4/2002 | Berthon-Jones et al. |
| 6,371,112 B1 | 4/2002 | Bibi |
| 6,397,845 B1 | 6/2002 | Burton |
| 6,398,739 B1 | 6/2002 | Sullivan et al. |
| 6,409,676 B2 | 6/2002 | Ruton et al. |
| 6,425,395 B1 | 7/2002 | Ruton et al. |
| 6,427,689 B1 | 8/2002 | Estes et al. |
| 6,477,408 B1 | 11/2002 | Turek et al. |
| 6,488,634 B1 | 12/2002 | Rapoport et al. |
| 6,511,424 B1 | 1/2003 | Moore-Ede et al. |
| 6,581,595 B1 | 6/2003 | Murdock et al. |
| 6,605,038 B1 | 8/2003 | Teller et al. |
| 6,629,527 B1 | 10/2003 | Estes et al. |
| 6,644,312 B2 | 11/2003 | Berthon-Jones et al. |
| 6,770,037 B2 | 8/2004 | Sullivan et al. |
| 6,805,668 B1 | 10/2004 | Cadwell |
| 6,845,773 B2 | 1/2005 | Berthon-Jones et al. |
| 6,889,691 B2 | 5/2005 | Eklund et al. |
| 6,890,306 B2 | 5/2005 | Poezevera |
| 6,988,994 B2 | 1/2006 | Rapoport et al. |
| 7,013,892 B2 | 3/2006 | Estes et al. |
| 7,041,049 B1 | 5/2006 | Raniere |
| 7,089,937 B2 | 8/2006 | Berthon-Jones et al. |
| 7,150,718 B2 | 12/2006 | Okada et al. |
| 7,186,221 B2 | 3/2007 | Rapoport et al. |
| 7,189,204 B2 | 3/2007 | Ni et al. |
| 7,204,250 B1 | 4/2007 | Burton |
| 7,207,947 B2 | 4/2007 | Koh et al. |
| 7,276,031 B2 | 10/2007 | Norman et al. |
| 7,429,247 B2 | 9/2008 | Okada et al. |
| 7,469,697 B2 | 12/2008 | Lee et al. |
| 7,572,225 B2 | 8/2009 | Stahmann et al. |
| 7,662,101 B2 | 2/2010 | Lee et al. |
| 7,717,848 B2 | 5/2010 | Heruth et al. |
| 7,770,578 B2 | 8/2010 | Estes et al. |
| 7,775,993 B2 | 8/2010 | Heruth et al. |
| 7,787,946 B2 | 8/2010 | Stahmann et al. |
| 7,896,812 B2 | 3/2011 | Rapoport et al. |
| 8,002,553 B2 | 8/2011 | Hatlestad et al. |
| 8,069,852 B2 | 12/2011 | Burton et al. |
| 8,192,376 B2 | 6/2012 | Lovett et al. |
| 8,281,787 B2 | 10/2012 | Burton |
| 8,333,708 B2 | 12/2012 | Rapoport et al. |
| 9,108,009 B2 | 8/2015 | Rapoport et al. |
| 9,168,344 B2 | 10/2015 | Rapoport et al. |
| 9,227,032 B2 | 1/2016 | Kwok et al. |
| 9,750,908 B2 | 9/2017 | Kuriger et al. |
| 10,099,026 B2 | 10/2018 | Rapoport et al. |
| 10,213,576 B2 | 2/2019 | Arrowsmith et al. |
| 10,471,230 B2 | 11/2019 | Harwood et al. |
| 2001/0000346 A1 | 4/2001 | Ruton |
| 2001/0027792 A1 | 10/2001 | Berthon-Jones |
| 2002/0014241 A1 | 2/2002 | Gradon et al. |
| 2002/0023645 A1 | 2/2002 | Zdrojkowski et al. |
| 2002/0029000 A1 | 3/2002 | Ohsaki |
| 2002/0185130 A1 | 12/2002 | Wright |
| 2002/0193697 A1 | 12/2002 | Cho et al. |
| 2003/0000528 A1 | 1/2003 | Eklund |
| 2004/0016433 A1 | 1/2004 | Estes et al. |
| 2004/0074497 A1 | 4/2004 | Berthon-Jones |
| 2005/0038353 A1 | 2/2005 | Rapoport |
| 2005/0080349 A1 | 4/2005 | Okada et al. |
| 2005/0113710 A1 | 5/2005 | Stahmann |
| 2005/0115561 A1 | 6/2005 | Stahmann |
| 2005/0133032 A1 | 6/2005 | Berthon-Jones |
| 2005/0217674 A1 | 10/2005 | Burton |
| 2005/0256420 A1 | 11/2005 | Norman |
| 2006/0009704 A1 | 1/2006 | Okada et al. |
| 2006/0009708 A1 | 1/2006 | Rapoport |
| 2006/0084877 A1 | 4/2006 | Ujhazy |
| 2006/0102179 A1 | 5/2006 | Rapoport |
| 2006/0118112 A1 | 6/2006 | Cattano et al. |
| 2006/0249149 A1 | 11/2006 | Meier et al. |
| 2007/0032733 A1 | 2/2007 | Burton |
| 2007/0055168 A1 | 3/2007 | Rapoport |
| 2008/0033304 A1 | 2/2008 | Dalal |
| 2008/0275349 A1* | 11/2008 | Halperin .............. A61B 5/0205 600/484 |
| 2011/0166470 A1 | 7/2011 | Rapoport et al. |
| 2011/0230779 A1* | 9/2011 | Titchener .............. A61B 5/087 600/538 |
| 2015/0038865 A1* | 2/2015 | Shigeto ................ A61B 5/1135 600/529 |
| 2015/0107594 A1 | 4/2015 | Rapoport et al. |
| 2015/0165147 A1 | 6/2015 | Rapoport et al. |
| 2015/0190086 A1* | 7/2015 | Chan .................... A61B 5/4812 600/301 |
| 2019/0232005 A1 | 8/2019 | Rapoport et al. |

FOREIGN PATENT DOCUMENTS

| | | |
|---|---|---|
| WO | WO 1994/023780 | 10/1994 |
| WO | WO 1997/016216 | 5/1997 |
| WO | WO 1997/028838 | 8/1997 |
| WO | WO 2002/000283 | 1/2002 |
| WO | WO 2002/028281 | 4/2002 |
| WO | WO 2002/094358 | 11/2002 |
| WO | WO 2003/008027 | 1/2003 |
| WO | WO 2003/057025 | 7/2003 |
| WO | WO 2005/018416 | 3/2005 |
| WO | WO 2011/006199 | 1/2011 |
| WO | WO 2014/047310 | 3/2014 |

* cited by examiner

FLOW-BASED SLEEP STAGE DETERMINATION

FIELD OF THE INVENTION

The invention relates to a method and system for sleep stage determination. More particularly the invention relates to sleep stage determination based at least partly on respiratory signal.

BACKGROUND OF THE INVENTION

Devices or systems for providing a humidified gases flow to a user for therapeutic purposes are well known in the art. Such devices are typically configured to detect Sleep Disordered Breathing (SDB) events. Such devices are not usually configured to obtain more detailed information about a user's sleep patterns. One example is the determination of sleep stage of a user.

Sleep stage is determined by the analysis of bio-signals including at least (electroencephalogram (eeg), electromyogram (emg), and electro-oculogram (eog). The definition of sleep stages is based on the characteristics of the bio-signals.

At the present time, the most accepted method to determine sleep stages requires the interaction from experienced sleep technicians, which analyses several traces of signals (PSG study).

It is an object of at least preferred embodiments of the present invention to address some of the aforementioned disadvantages. An additional or alternative object is to at least provide the public with a useful choice.

SUMMARY OF THE INVENTION

In one aspect a method of determining a sleep stage of a user comprises receiving a respiratory flow signal of a user; obtaining at least one respiratory feature from at least part of the respiratory flow signal; and determining a sleep stage from the at least one respiratory feature.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

Preferably the at least one respiratory feature is based at least partly on at least one duration measurement.

Preferably the at least one duration measurement includes one or more of breath duration, inspiration duration, maximum inspiration time, maximum expiration time, a function of maximum expiration time and maximum inspiration time, a function of inspiration duration and breath duration.

Preferably the at least one respiratory feature is based at least partly on at least one amplitude measurement.

Preferably the at least one amplitude measurement includes one or more of maximum inspiration amplitude, maximum expiration amplitude, a function of maximum inspiration amplitude and maximum expiration amplitude.

Preferably the at least one respiratory feature is based at least partly on at least one centre of mass related measurement.

Preferably the at least one centre of mass related measurement includes one or more of inspiration centre of mass time, inspiration centre of mass amplitude, expiration centre of mass time, expiration centre of mass amplitude, a function of expiration centre of mass time and inspiration centre of mass time, a function of expiration centre of mass amplitude and inspiration centre of mass amplitude.

Preferably the at least one respiratory feature is based at least partly on at least one derivative related measurement.

Preferably the at least one derivative related measurement includes one or more of maximum negative acceleration time, maximum negative acceleration amplitude, maximum positive acceleration time, maximum positive acceleration amplitude, maximum negative flow rate time, maximum negative flow rate amplitude, maximum inspiration acceleration time, maximum inspiration acceleration amplitude.

Preferably the at least one respiratory feature is based at least partly on at least one volume related measurement.

Preferably the at least one volume related measurement includes one or more of inspiration volume, expiration volume, a function of inspiration volume and expiration volume.

Preferably the method further comprises identifying, within the respiratory flow signal, at least one breath signal representing a breath of the user; and obtaining at least one breath measurement from a portion of the respiratory flow signal within which the at least one breath signal is identified.

Preferably the method further comprises identifying, within the respiratory flow signal, a window containing a plurality of breath signals; and obtaining respective breath measurements of the breath signals within the window.

Preferably the at least one breath feature comprises a mean and/or standard deviation of the breath measurements within at least part of the window.

Preferably the method further comprises determining a sleep stage from the at least one breath feature at least partly by applying at least one of a supervised learning algorithm, an unsupervised learning algorithm, a semi-supervised learning algorithm.

Preferably the at least one supervised learning algorithm comprises one or more of linear and logistic regression, support vector machine, artificial neural network, decision tree.

Preferably the sleep stage comprises one of awake, N1, N2, N3, REM.

Preferably the sleep stage comprises one of awake, light sleep, deep sleep, REM.

Preferably the sleep stage comprises one of awake, non-REM, REM.

Preferably the sleep stage comprises one of awake, sleep.

Preferably the method further comprises applying a filter to the respiratory flow signal to remove at least one of high frequency noise, DC level.

In another aspect, a sleep determination system comprises a feature extractor configured to obtain at least one respiratory feature from at least part of a respiratory flow signal of a user; and a mapping module configured to determine a sleep stage from the at least one respiratory feature.

In another aspect, a sleep determination system comprises a processor; and a computer readable medium having stored thereon computer executable instructions that, when executed by the processor, cause the processor to perform a method of determining a sleep stage of a user. The method comprises receiving a respiratory flow signal of a user; obtaining at least one respiratory feature from at least part of the respiratory flow signal; and determining a sleep stage from the at least one respiratory feature.

In another aspect, a computer readable medium has stored thereon computer-executable instructions that, when executed by a processor, cause the processor to perform a method of determining a sleep stage of a user. The method comprises receiving a respiratory flow signal of a user; obtaining at least one respiratory feature from at least part of the respiratory flow signal; and determining a sleep stage from the at least one respiratory feature.

The invention in one aspect comprises several steps. The relation of one or more of such steps with respect to each of the others, the apparatus embodying features of construction, and combinations of elements and arrangement of parts that are adapted to affect such steps, are all exemplified in the following detailed disclosure.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

As used herein, '(s)' following a noun means the plural and/or singular forms of the noun.

As used herein, the term 'and/or' means 'and' or 'or' or both.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9, and 10) and also any range of rational numbers within that range (for example, 2 to 8, 1.5 to 5.5, and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents or such sources of information is not to be construed as an admission that such documents or such sources of information, in any jurisdiction, are prior art or form part of the common general knowledge in the art.

Although the present invention is broadly as defined above, those persons skilled in the art will appreciate that the invention is not limited thereto and that the invention also includes embodiments of which the following description gives examples.

The term 'connected to' as used in this specification in relation to data or signal transfer includes all direct or indirect types of communication, including wired and wireless, via a cellular network, via a data bus, or any other computer structure. It is envisaged that they may be intervening elements between the connected integers. Variants such as 'in communication with', 'joined to', and 'attached to' are to be interpreted in a similar manner. Related terms such as 'connecting' and 'in connection with' are to be interpreted in the same manner.

The term 'computer-readable medium' should be taken to include a single medium or multiple media. Examples of multiple media include a centralised or distributed database and/or associated caches. These multiple media store the one or more sets of computer executable instructions. The term 'computer readable medium' should also be taken to include any medium that is capable of storing, encoding or carrying a set of instructions for execution by a processor and that cause the processor to perform any one or more of the methods described above. The computer-readable medium is also capable of storing, encoding or carrying data structures used by or associated with these sets of instructions. The term 'computer-readable medium' includes solid-state memories, optical media and magnetic media.

BRIEF DESCRIPTION OF THE DRAWINGS

Preferred forms of the method and system for sleep stage determination will now be described by way of example only with reference to the accompanying figures in which.

DETAILED DESCRIPTION

Figure 1:
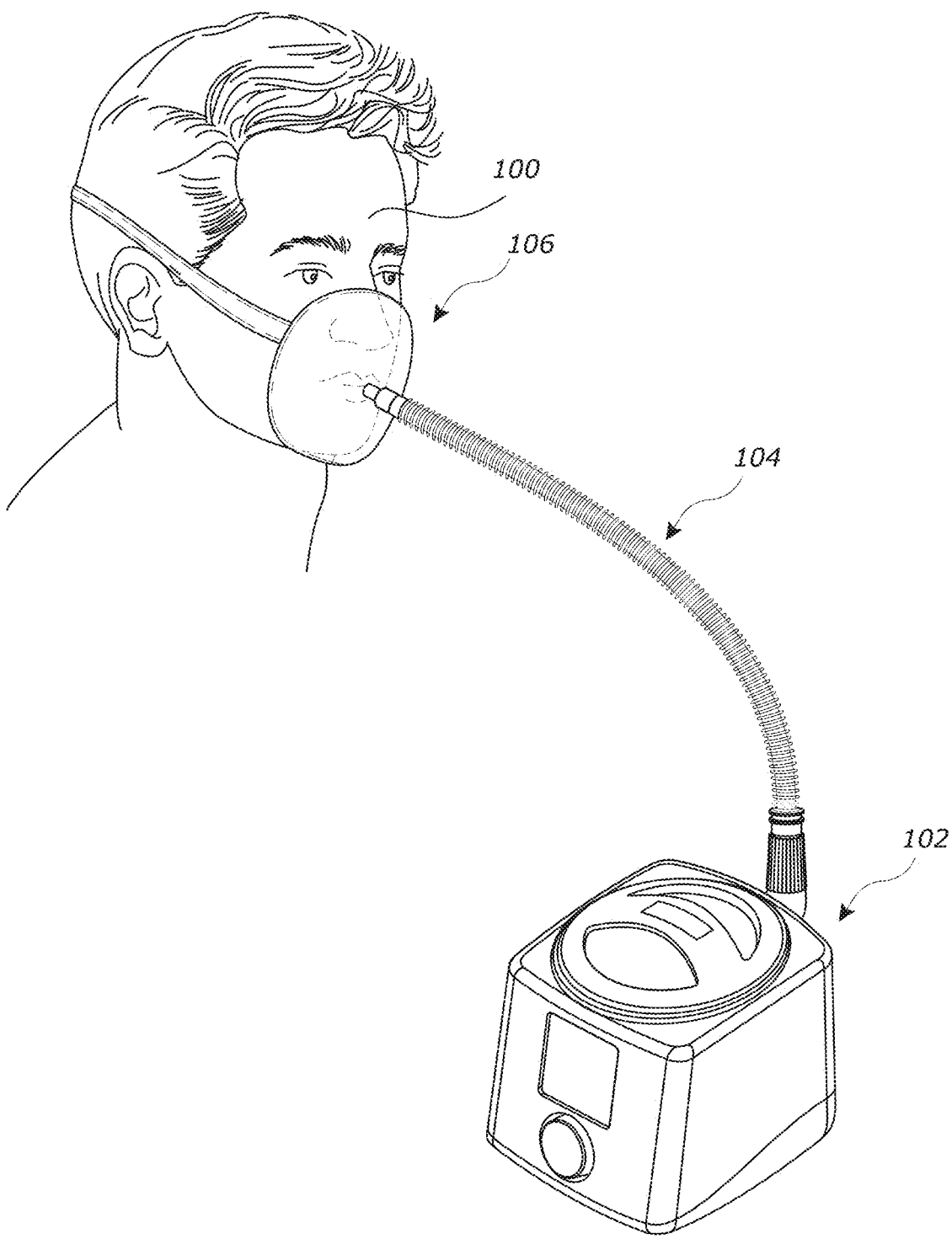
FIG. 1 is a perspective view of a Continuous Positive Airway Pressure (CPAP) machine configured to obtain a respiratory flow signal from a user.

FIG. 1 shows a user 100 receiving air from a modular assisted breathing unit and humidifier system 102. System 102 is shown in FIG. 1 as a Continuous Positive Airway Pressure (CPAP) machine. In an embodiment the system 102 provides a pressurised stream of heated, humidified gases to the user 100 for therapeutic purposes. These therapeutic purposes include for example one or more of reducing the incidence of obstructive sleep apnea, providing CPAP therapy, providing humidification for therapeutic purposes.

A heated and humidified gases stream passes along the length of a delivery conduit 104 and are provided to the user 100 via a user interface 106. In an embodiment the conduit 104 is heated via a heater wire (not shown) or similar to help prevent rain-out.

The conduit 104 typically has a circular internal cross-section. The internal diameter of the conduit is typically about 20 mm. in an embodiment the internal diameter is between 10 mm and 30 mm. These typical dimensions apply to both flexible portions of the gases flow passageway and rigid components such as elbows and connectors and portions integrated into components of the humidified gases supply.

In an embodiment the user interface 106 comprises a full face mask. It will be appreciated that alternatives to a full face mask include a nasal mask that surrounds and covers the nose of the user 100, nasal cannula, tracheostomy fitting, any other suitable user interface.

Figure 2:
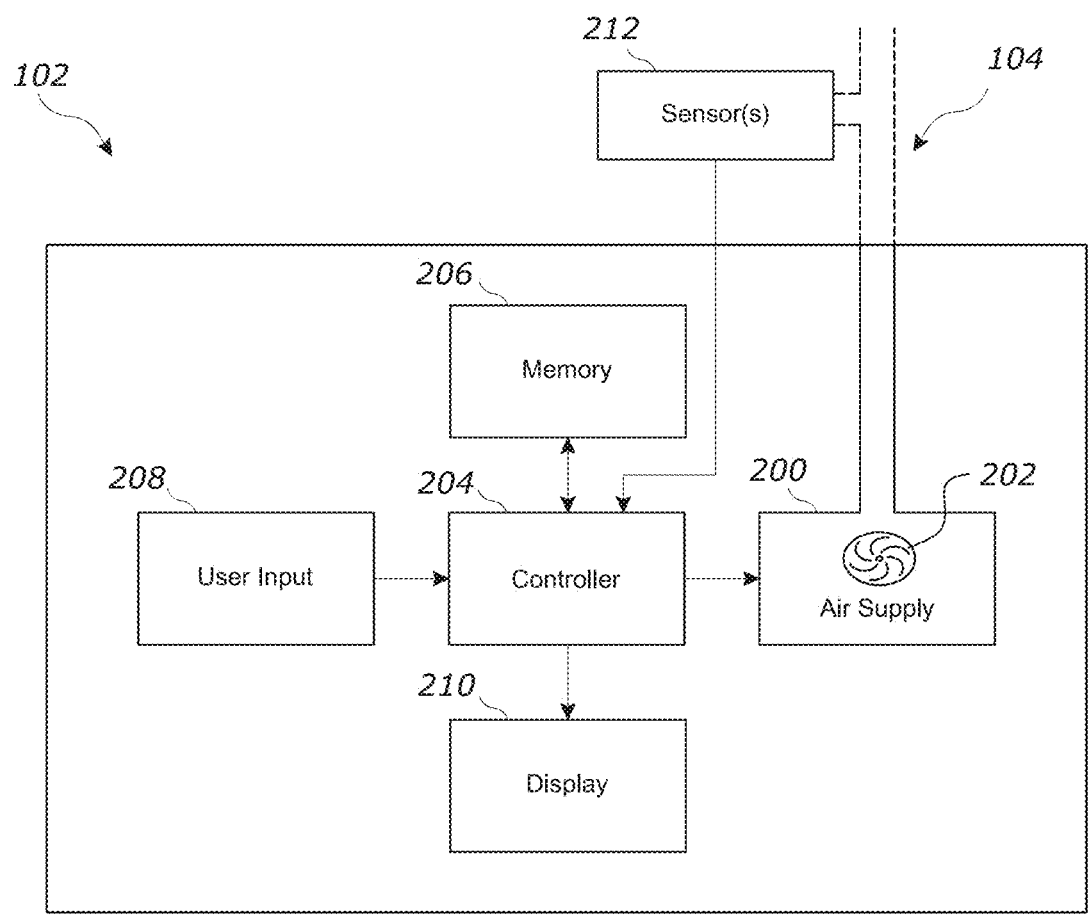
FIG. 2 shows a schematic view of the CPAP machine of FIG. 1.

FIG. 2 shows a schematic view of system 100 of FIG. 1. The system 100 includes an air supply 200 configured to deliver the heated and humidified gases stream into the delivery conduit 104.

In an embodiment the air supply 200 includes a flow control mechanism that in turn includes for example an internal compressor unit and a flow generator or fan unit 202. Air from the atmosphere enters the housing of the air supply 200 via an atmospheric inlet (not shown) and is drawn through the fan unit 202. In an embodiment the output of the fan unit 202 is adjustable by varying the speed of the fan.

In an embodiment the air supply 200 includes or is interfaced to a humidifier chamber (not shown). The humidifier chamber contains a volume of water. A heater plate heats the base of the humidifier chamber thereby heating the contents of the chamber. As the water in the chamber is heated it evaporates and the gases within the humidifier chamber become heated and humidified. The gases stream entering the humidifier chamber passes over the heated water and becomes heated and humidified as it does so.

As described above the heated and humidified gases stream enters the delivery conduit 104.

A central controller 204 or control system is connected to a memory 206. The controller 204 receives user input signals via user input 208 and displays output to a user via display 210. In an embodiment the controller 204 receives input from at least one sensor 212 located at various points within system 102, conduit 104 and/or interface 106. In response to the input from user input 208 and sensor(s) 212 the controller 204 determines a control output that sends signals to adjust the power to the air supply 202.

In an embodiment the sensor(s) 212 receive signals representative of inspiration and expiration of the user 100. The sensor(s) 212 sends a respiratory flow signal to the controller 204.

Figure 3:
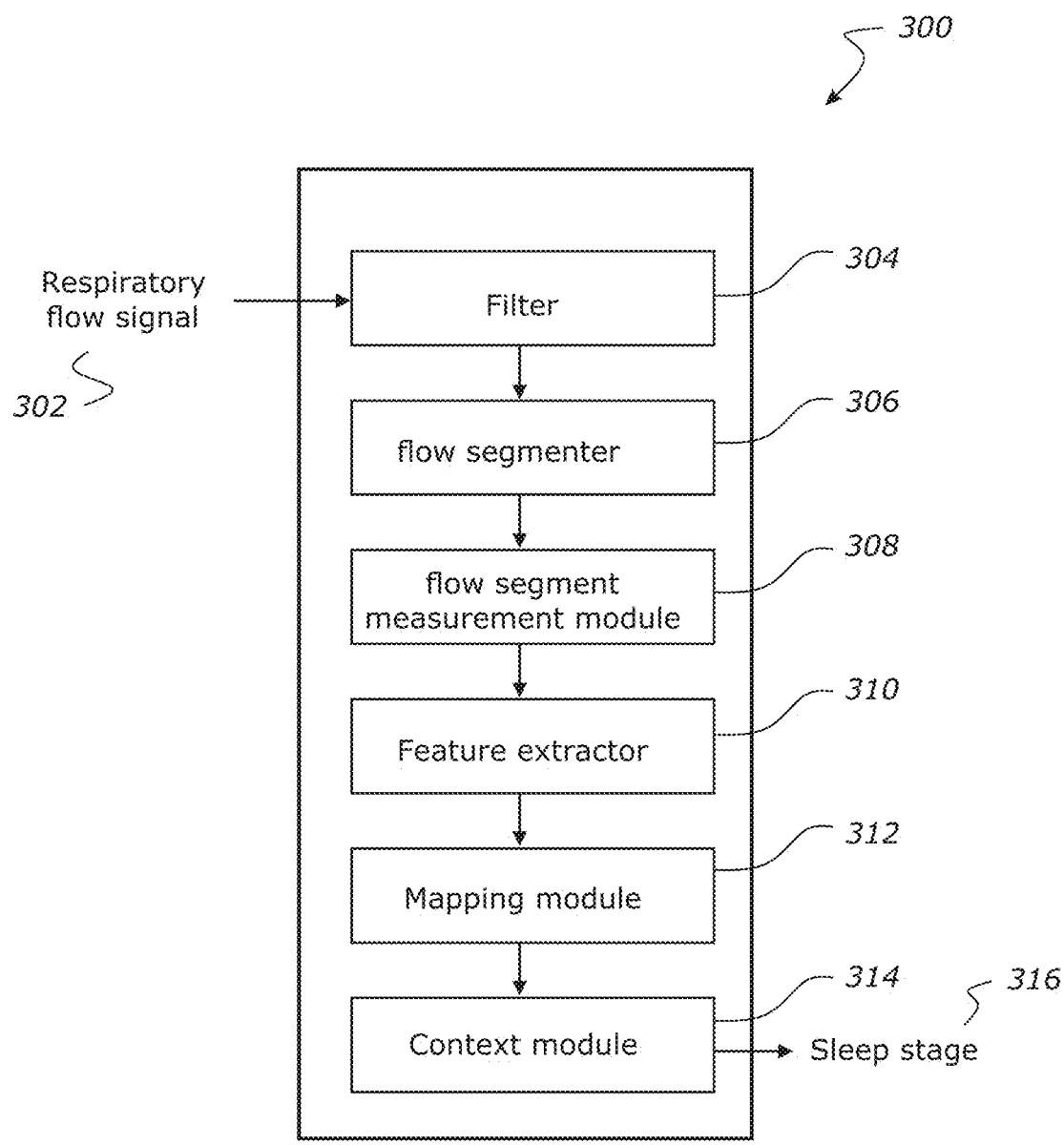
FIG. 3 shows a schematic view of a sleep stage determination module.

FIG. 3 shows a schematic view of a sleep stage determination module 300. The module 300 receives a respiratory flow signal 302. An example of a respiratory flow signal is one sent from the sensor(s) 212 to the controller 204.

In an embodiment a filter 304 pre-processes the respiratory flow signal to remove high frequency noise and DC level. The use of the filter 304 is optional. In an embodiment the filter 304 is not present or the respiratory flow signal 302 is not sent to the filter 304.

In an embodiment a flow segmenter 306 segments the respiratory flow signal into time-based epochs and/or breath-number-based epochs for subsequent feature extraction as will be further described below. The use of the flow segmenter 306 is optional. In an embodiment feature extraction is performed on the raw respiratory flow signal 302.

In an embodiment a flow segment measurement module 308 determines measurements of the respiratory flow signal 302 on which feature extraction is subsequently based as will be described below. In an embodiment the measurement module 308 determines one or more of duration measurements, amplitude measurements, centre of mass related measurements, derivative related measurements, volume related measurements.

In an embodiment a feature extractor 310 obtains at least one respiratory feature from the respiratory flow signal 302. As described above the feature extractor takes as input one or more of a filtered respiratory flow signal, a segmented respiratory flow signal in which breath segmentation has been performed, an otherwise unprocessed respiratory flow signal.

In an embodiment a mapping module 312 maps a set of respiratory features to at least one sleep stage as will be further described below. A context module 314 optionally applies context data in an attempt to improve the accuracy of the mapping module 312 output.

The module 300 outputs a sleep stage 316 determined by the mapping module 312 and optionally context module 314 from the respiratory flow signal 302. In an embodiment the module determines a sequence of and/or multiple sleep stages 316 from a respiratory flow signal 302.

In an embodiment the module 300 is implemented within the modular assisted breathing unit and humidifier system 102. The module outputs the sleep stage 316 on the display 210 and/or stores the sleep stage on the memory 206.

Figure 14:
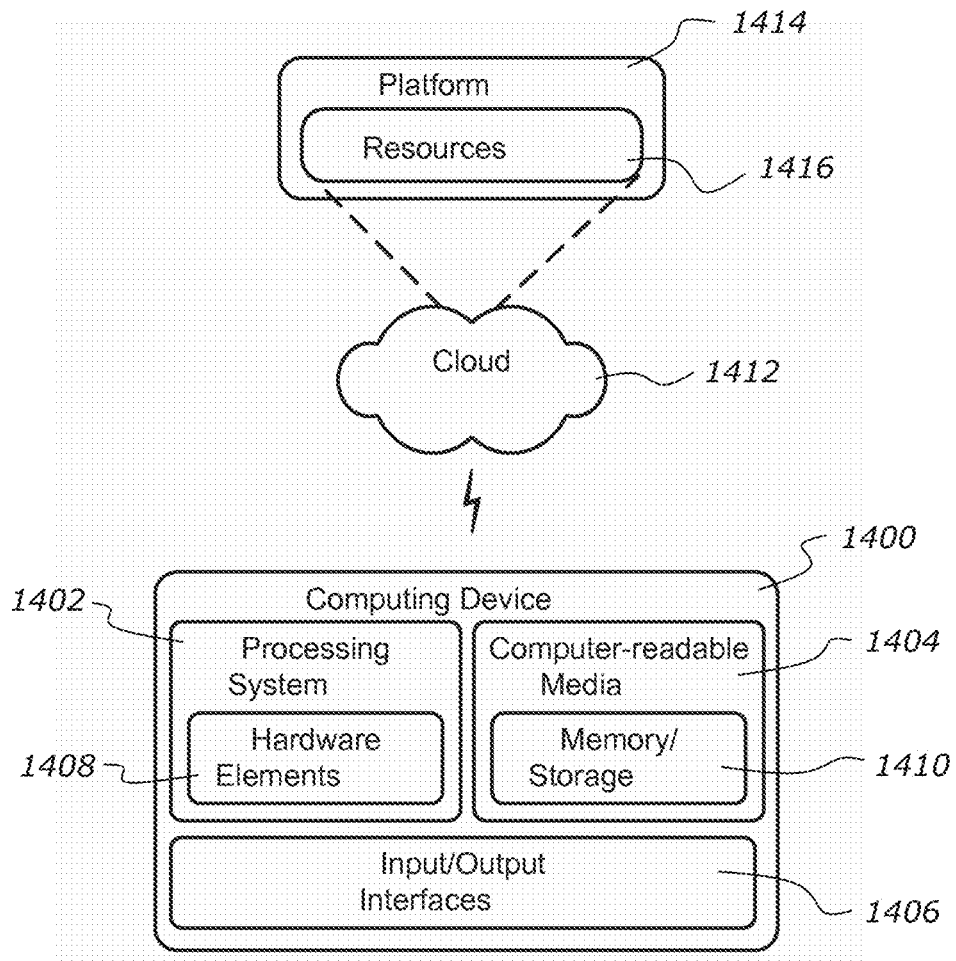
FIG. 14 shows an example of a computing system and/or device that implements the sleep stage determination module of FIG. 3.

In an embodiment the module 300 is implemented on a computing device for example the computing device 1400 of FIG. 14. The sleep stage 316 is presented on a display and/or maintained on a memory that either form(s) part of the computing device 1400 or is/are connected to computing device 1400.

Figure 4:
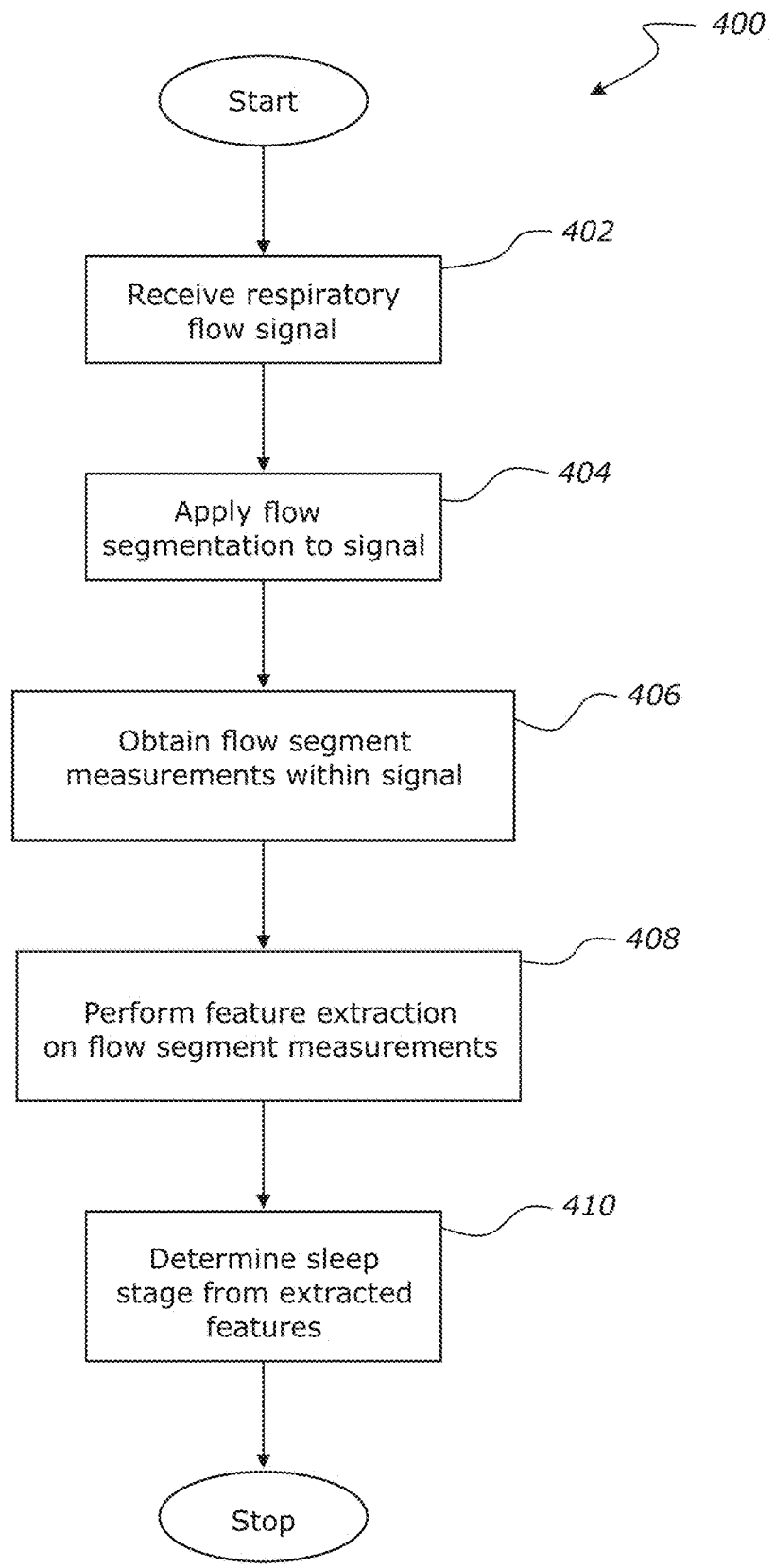
FIG. 4 shows an example of a method performed by the sleep stage determination module of FIG. 3.

FIG. 4 shows an example of a method 400 performed by the sleep stage determination module 300 of FIG. 3. In an embodiment, the module 300 receives 402 a respiratory flow signal. Filtering (not shown) is optionally performed on the respiratory flow signal to remove high frequency noise and DC level.

In an embodiment the flow segmenter 306 of FIG. 3 optionally applies 404 flow segmentation to the respiratory flow signal. As described above, the flow segmenter segments the respiratory flow signal into time-based epochs and/or breath-number-based epochs for subsequent feature extraction.

In an embodiment the measurement module 308 obtains 406 flow segment measurements of the respiratory flow signal on which feature extraction is subsequently based. Examples of measurements include one or more of duration measurements, amplitude measurements, centre of mass related measurements, derivative related measurements, volume related measurements. In an embodiment these measurements comprise breath measurements.

In an embodiment the feature extractor 310 performs 408 feature extraction on flow segment measurements. For example, the feature extractor 310 obtains at least one respiratory feature from the respiratory flow signal.

The module 300 determines 410 a sleep stage, a sequence of sleep stages, and/or multiple sleep stages from the features extracted from the respiratory flow signal. In an embodiment this function is performed by the mapping module 312 and optionally also the context module 314.

Figure 5:
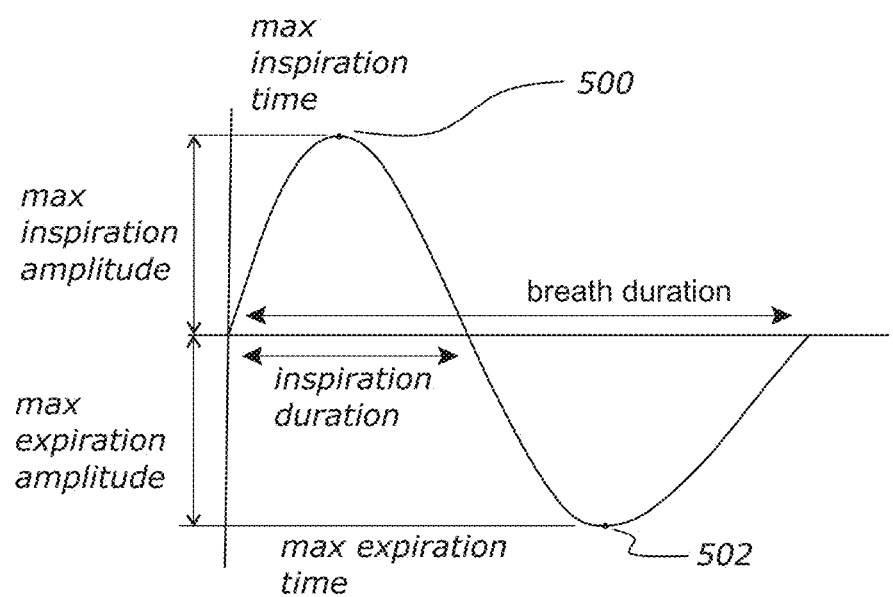
FIG. 5 shows examples of duration measurements and amplitude measurements from which the feature extractor of FIG. 3 obtains respiratory feature(s).

In an embodiment, the feature extractor obtains at least one respiratory feature based at least partly on at least one duration measurement. FIG. 5 shows examples of duration measurements associated to a maximum inspiration 500 and a maximum expiration 502.

In an embodiment, the duration measurements include one or more of:
breath duration
inspiration duration
maximum inspiration time
maximum expiration time In an embodiment, the duration measurements include a function of two or more duration measurements. Examples of functions include:
a difference between maximum expiration time and maximum inspiration time
a ratio of inspiration duration to breath duration.

In an embodiment, the feature extractor obtains at least one respiratory feature based at least partly on at least one amplitude measurement. FIG. 5 also shows examples of amplitude measurements.

In an embodiment, the amplitude measurements include one or more of:
maximum inspiration amplitude
maximum expiration amplitude.

In an embodiment, the amplitude measurements include a function of two or more amplitude measurements. An example of a function is a difference between maximum inspiration amplitude and maximum expiration amplitude.

In an embodiment the duration and/or amplitude measurements are obtained from a single breath. In an embodiment the duration and/or amplitude measurements are calculated as a mean or average of at least two breaths. In an embodiment the at least two breaths are consecutive.

Figure 6:
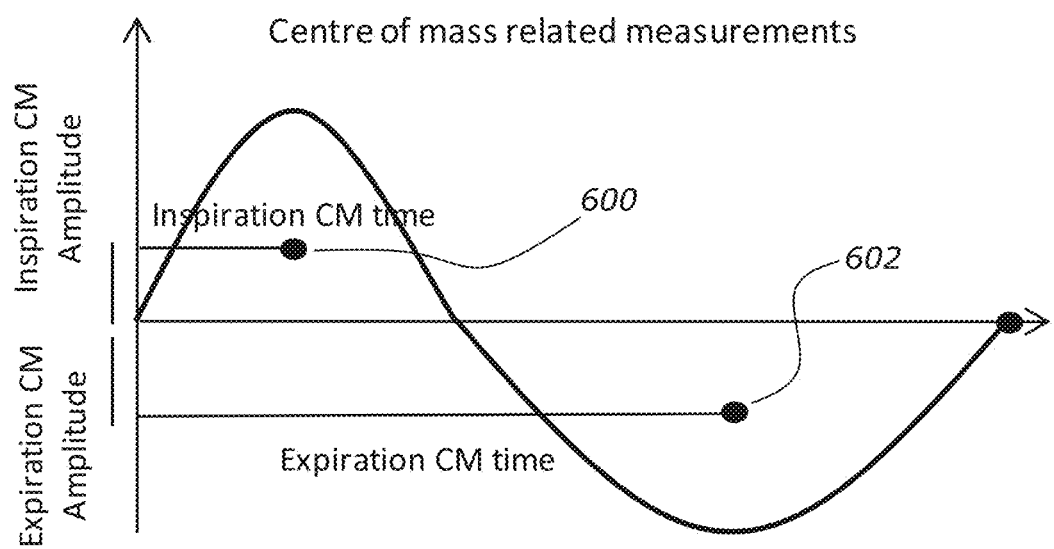
FIG. 6 shows examples of centre of mass measurements from which the feature extractor obtains respiratory feature (s).

In an embodiment, the feature extractor obtains at least one respiratory feature based at least partly on at least one centre of mass measurement. FIG. 6 shows examples of centre of mass measurements.

In an embodiment, the centre of mass measurement includes inspiration centre of mass time. The centre of mass of the body formed by the inspiration curve is indicated at 600. A time axis component of the inspiration centre of mass 600 is calculated for example relative to the beginning of the breath by the following:

$$x_{cm} = \frac{\sum_{i=1}^{Ninsp} |(y_i(x_i - x_{i-1}))|x_i}{\sum_{i=1}^{Ninsp} |(y_i(x_i - x_{i-1}))|}$$

where $N_{Insp}$ is the number of inspiration points i in the curve, $y_i$ and $x_i$ are the signal amplitudes and time, respectively.

In an embodiment, the centre of mass measurement includes expiration centre of mass time. The centre of mass of the body formed by the inspiration curve is indicated at 602. A time axis component of the expiration centre of mass 602 is calculated for example relative to the beginning of the breath by the following:

$$x_{cm} = \frac{\sum_{i=1}^{NExp} |(y_i(x_i - x_{i-1}))|x_i}{\sum_{i=1}^{NExp} |(y_i(x_i - x_{i-1}))|}$$

where $N_{Exp}$ is the number of expiration points i in the curve, $y_i$ and $x_i$ are the signal amplitude and time respectively.

In an embodiment, the centre of mass measurement includes a function of expiration centre of mass time and inspiration centre of mass time. An example is the difference between expiration centre of mass time and inspiration centre of mass time.

In an embodiment, the centre of mass measurement includes inspiration centre of mass amplitude. An amplitude axis component of the inspiration centre of mass 600 is calculated for example relative to the inspiration curve and the baseline by the following:

$$y_{cm} = \frac{\sum_{i=1}^{Ninsp} |(y_i(x_i - x_{i-1}))|y_i}{2 \sum_{i=1}^{Ninsp} |(y_i(x_i - x_{i-1}))|}$$

where $N_{Isp}$ is the number of inspiration points i in the curve, $y_i$ and $x_i$ are the signal amplitude and time, respectively.

In an embodiment, the centre of mass measurement includes expiration centre of mass amplitude. An amplitude axis component of the expiration centre of mass 602 is calculated for example relative to the expiration curve and the baseline by the following:

$$y_{cm} = \frac{\sum_{i=1}^{NExp} |(y_i(x_i - x_{i-1}))|y_i}{2 \sum_{i=1}^{NExp} |(y_i(x_i - x_{i-1}))|}$$

where $N_{Exp}$ is the number of expiration points i in the curve, $y_i$ and $x_i$ are the signal amplitude and time, respectively.

In an embodiment, the centre of mass measurement includes a function of expiration centre of mass amplitude and inspiration centre of mass amplitude. An example is the difference between expiration centre of mass amplitude and inspiration centre of mass amplitude.

Figure 7:
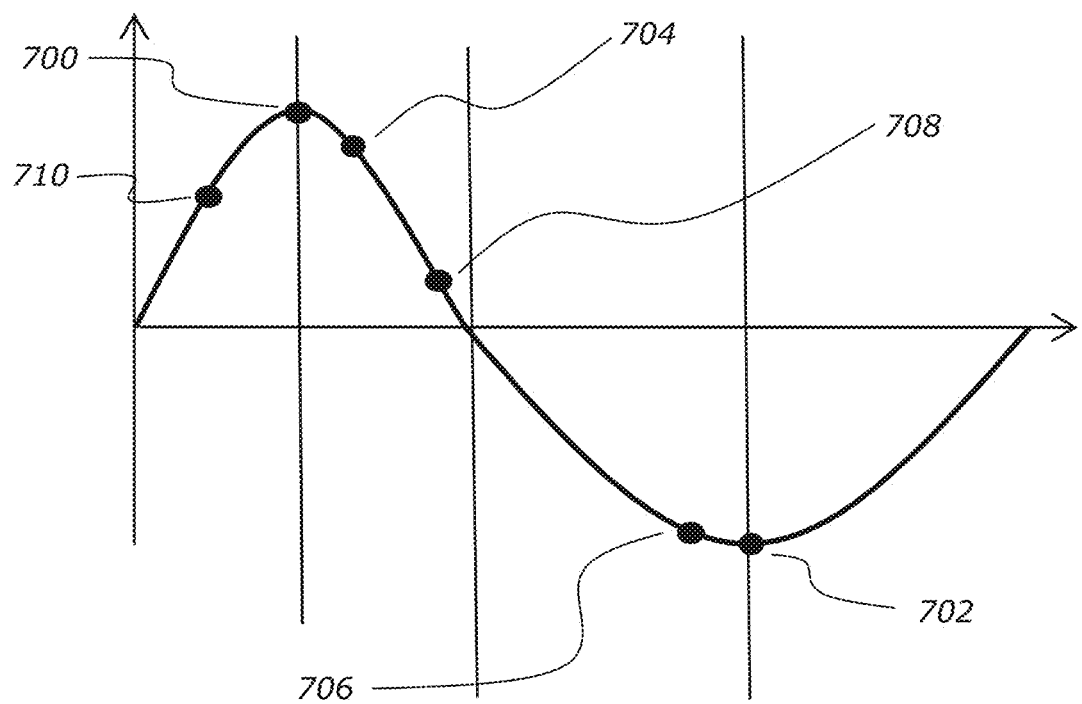
FIG. 7 shows examples of derivative related measurements from which the feature extractor obtains respiratory feature(s).

In an embodiment, the feature extractor obtains at least one respiratory feature based at least partly on at least one derivative related measurement. FIG. 7 shows examples of derivative related measurements.

In an embodiment, the derivative related measurement includes a maximum negative acceleration time. FIG. 7 shows a maximum inspiration 700 and a maximum expiration 702. A maximum negative acceleration 704 has a time value between the time of maximum inspiration 700 and the time of maximum expiration 702. The time value of 704 is a time when the acceleration reaches a negative peak, calculated from the beginning of the breath. In an embodiment the time value is computed with the second derivative obtained from a Savitzky Golay filter.

In an embodiment, the derivative related measurement includes a maximum positive acceleration time, having a time value between the time of maximum inspiration 700 and the time of maximum expiration 702. The time value of 706 is a time when the acceleration reaches a positive peak, calculated from the beginning of the breath. In an embodiment the time value of 706 is computed with the second derivative obtained from a Savitzky Golay filter.

In an embodiment, the derivative related measurement includes a time value for a maximum inspiration acceleration 710. A time value for maximum inspiration acceleration 710 is a time value between the start of the breath and maximum inspiration 700 when the acceleration is at a maximum. In an embodiment the time value is computed with the second derivative obtained from a Savitzky Golay filter.

In an embodiment the derivative related measurement includes a function of a maximum negative acceleration time and a maximum positive acceleration time. An example is a maximum negative flow rate time 708 comprising a time between maximum negative acceleration and maximum positive acceleration when the acceleration is zero, calculated from the beginning of the breath. In an embodiment this is computed by finding a first zero crossing position on a second derivative signal generated by a Savitsky Golay filter.

In an embodiment, the derivative related measurement includes a maximum negative acceleration amplitude. The amplitude of the maximum negative acceleration 704 occurs between a time of maximum inspiration 700 and a time of maximum expiration 702. In an embodiment the amplitude of maximum negative acceleration 704 is computed with the second derivative obtained from a Savitzky Golay filter.

In an embodiment, the derivative related measurement includes a maximum positive acceleration amplitude. The amplitude of the maximum positive acceleration 706 occurs between a time of maximum negative acceleration 704 and the end of the breath. In an embodiment the amplitude of maximum positive acceleration 706 is computed with the second derivative obtained from a Savitzky Golay filter.

In an embodiment, the derivative related measurement includes an amplitude for the maximum inspiration acceleration 710. The amplitude occurs between the start of the breath and maximum inspiration 700. In an embodiment the amplitude is computed with the second derivative obtained from a Savitzky Golay filter.

In an embodiment the derivative related measurement includes a function of a maximum negative acceleration time and a maximum positive acceleration time. An example is an amplitude of maximum negative flow rate 708 comprising an amplitude of a maximum rate of change in the flow signal that occurs between maximum negative acceleration and maximum positive acceleration. In an embodiment the amplitude is approximated by calculating the difference in flow at the point when the acceleration is zero.

Figure 8:
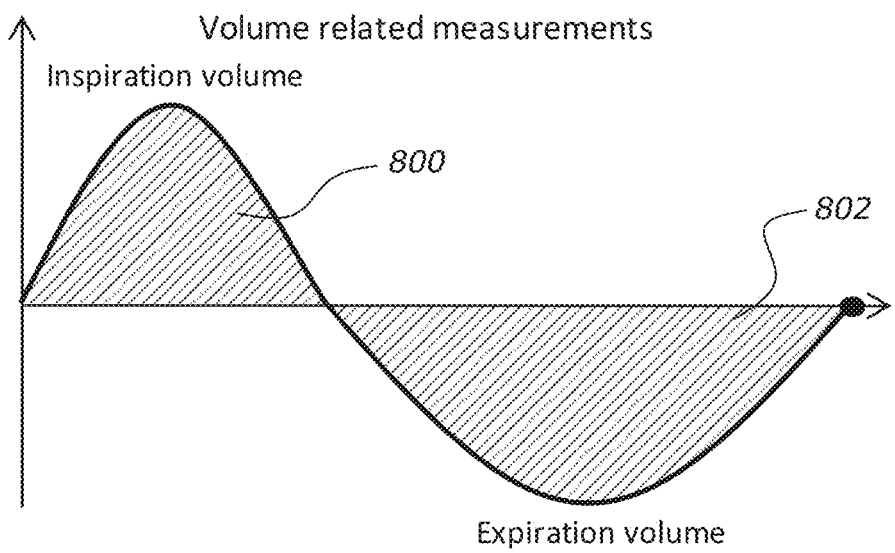
FIG. 8 shows examples of volume related measurements from which the feature extractor obtains respiratory feature (s).

In an embodiment, the feature extractor obtains at least one respiratory feature based at least partly on at least one volume related measurement. FIG. 8 shows examples of volume related measurements.

In an embodiment, the volume related measurement includes inspiration volume 800 comprising the volume of the inspiration part of the flow signal above the baseline. The inspiration volume 800 is calculated for example by the following:

$$V_{Insp} = \frac{\sum_{i=1}^{NInsp}(y_i - B)}{SR}$$

where $N_{Insp}$ is the number of inspiration points i in the curve, $y_i$ and B are the signal amplitude and the baseline, respectively. SR is the sampling rate of the signal in samples per minute.

In an embodiment, the volume related measurement includes expiration volume 802 comprising the volume of the inspiration part of the flow signal above the baseline. The expiration volume 802 is calculated for example by the following:

$$V_{Exp} = \frac{\sum_{i=1}^{NExp}(y_i - B)}{SR}$$

where $N_{Exp}$ is the number of expiration points i in the curve, $y_i$ and B are the signal amplitude and the baseline, respectively. SR is the sampling rate of the signal in samples per minute.

In an embodiment, the volume related measurement includes a function of inspiration volume and expiration volume. An example is a ratio between inspiration volume and expiration volume.

Figure 9:
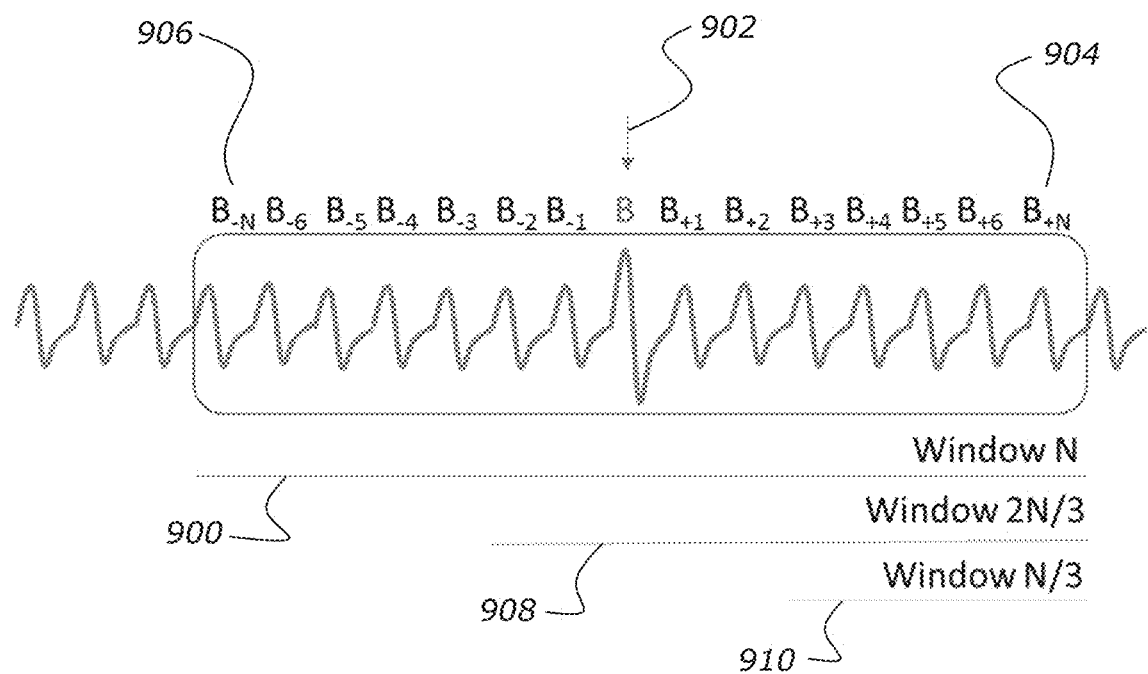
FIG. 9 shows an example of the feature extractor obtaining respiratory feature(s) from window(s) comprising multiple breath signals.

FIG. 9 shows an example of feature extraction that in an embodiment is performed by the feature extractor 310 of FIG. 3. A window 900 comprises a plurality of breath signals within a respiratory flow signal. Window 900 is shown centred on breath B indicated at 902.

In an embodiment the window is of size N so that it includes N consecutive breaths immediately following breath B in the respiratory flow signal, and includes N consecutive breaths immediately preceding breath B in the respiratory flow signal. The boundaries of window 900 are defined so as to include breath$_{+N}$ indicated at 904, and breath$_{-N}$ indicated at 906.

In an embodiment the value of N is 15. In an embodiment the value of N is selected from a range of 2 to 30.

In an embodiment the window 900 is further subdivided into at least one further window, for example window 908 and window 910. In an embodiment window 908 is ⅔ the size of window 900. In an embodiment window 910 is ⅓ the size of window 900.

In an embodiment, window 908 and/or window 910 has/have boundaries defined so as to include breath B and breath$_{+N}$ but not breath$_{-N}$. In an embodiment, window 908 and/or window 910 has/have boundaries defined so as to include breath B and breath-N but not breath$_{+N}$. In an embodiment, window 908 and/or window 910 has/have boundaries defined so as to include breath B but not breath$_{+N}$ and not breath$_{-N}$.

One example of a respiratory feature obtained from at least part of the respiratory flow signal is a mean breath measurement associated to at least some of the breaths in the respiratory flow signal.

In an embodiment the respiratory features obtained from the respiratory flow signal represent a mean breath measurement associated to the breaths within one or more of window 900, window 908, window 910.

Another example of a respiratory feature obtained from at least part of the respiratory flow signal is a standard deviation of breath measurements associated to at least some of the breaths in the respiratory flow signal.

In an embodiment the respiratory features obtained from the respiratory flow signal represent a standard deviation of breath measurements associated to the breaths within one or more of window 900, window 908, window 910.

In an embodiment the breath measurements include one or more of duration measurements, amplitude measurements, centre of mass related measurements, derivative related measurements, volume related measurements.

In an embodiment the breath features describe the morphology of part of the respiratory flow signal that surrounds a breath B under evaluation. In an embodiment the mean and/or standard deviation for up to 26 breath measurements are determined for one or more of windows 900, 908, 910. This results in a total of up to 156 respiratory features.

In an embodiment, a mapping is performed by the mapping module 312 of FIG. 3. The mapping module 312 is configured to map a given set of respiratory features to a sleep stage.

In an embodiment the mapping module 312 applies a supervised learning algorithm. Suitable algorithms include one or more of linear and logistic regression, support vector machine, artificial neural network, decision tree. In an embodiment, the learning is performed offline with previously recorded and labelled data.

In an embodiment the mapping module 312 applies an unsupervised learning algorithm. In an embodiment the mapping module 312 applies a semi-supervised learning algorithm.

In an embodiment, machine learning methods that provide such learning capabilities are used to improve accuracy of the module 300. In an embodiment, learning is carried out to suit the conditions of individual patients. For instance, parts of the signal where strong markers are present, for example start of the night or periods prior to events, can be used to adapt the model to specific patient profiles.

In an embodiment the mapping module 312 maps a set of respiratory features to a sleep stage selected from awake, N1, N2, N3, REM. In an embodiment the sleep stage is selected from awake, light sleep, deep sleep, REM. In an embodiment the sleep stage is selected from awake, non-REM, REM. In an embodiment the sleep stage is selected from awake, sleep.

In an embodiment the features are calculated on a breath basis. In this case the module 300 provides breath-basis output. The breath outputs are then combined in 30 second epochs to calculate agreement to a correct hypnogram determined by mapping module 312. The resultant epoch output for each class is calculated as the average of breaths output. The resultant epoch output is then normalized so that the sum of the outputs for all classes are 1.

In an embodiment a context module 314 is configured to apply contextual clues in an attempt to improve accuracy of the mapping module 312.

One example of a contextual clue is identification of periods without breathing. It can be assumed that a user is awake after long periods in which the absence of a respiratory flow signal is detected. This occurs in the beginning of the session and when the user takes the mask off during the night. An example threshold is 7 minutes. After this threshold period of no respiratory flow signal it is assumed the user is awake and a sleep stage of awake is determined.

Another example of a contextual clue is identification of Sleep Disordered Breathing (SDB) events. It is assumed that prior to the detection of SDB events, the user is asleep. Prior to SDB events, a sleep stage of sleep is set. This could be light, deep, or REM. In an embodiment a threshold window of 10 epochs (5 minutes) prior to an SDB event is used.

Another example of a contextual clue is neighbouring consensus. It is assumed that individual epochs with differing labels compared to their neighbouring epochs are wrongly detected. One aim is to remove sleep stages that are likely to have been wrongly detected, by analysing the context where they are placed.

In an embodiment, the modelling of sleep stages is performed using algorithms that learn temporal structures at different scales. Hidden Markov Models (HMM) and its state machine representation and Temporal Delay Neural Networks (TDNN) are examples of learning methods that can be used. In an embodiment, HMM is applied in an attempt to learn the sleep stage transition probabilities using several bio-signals. In an embodiment, 'a priori' probability is implemented to capture probabilities of observing a particular state at different periods of the night.

In an embodiment, the module 300 implements a sleep score. The sleep score attempts to capture, in at least one index, sleep quality and effectiveness. In an embodiment, multiple indices are used.

There is no clear consensus about the best metrics to capture quality of sleep. One reason for this is that the requirements for having a good night of sleep can vary from person to person, due to age, external factors, etc. Some metrics have been proposed, each one capturing the sleep condition in different ways. Some of these metrics are:

Sleep efficiency—Sleep efficiency is defined as Total Sleep time/Total time in bed. It captures the amount of time effectively sleeping while in bed.

Deep sleep time—Periods of deep sleep are when the body relaxes and are usually associated with body and muscular recovery (physical restoration).

REM time—Period of REM time are usually associated memory and learning consolidation.

Sleep fragmentation—Can be defined in different ways, but essentially tries to capture the number of times arousals/awakes occur during the night. Highly fragmented sleep is usually associated with poor sleep and difficulty to remain in deep sleep or REM stage for long periods.

A good night of sleep should ideally have long periods of deep sleep and REM stages and low sleep fragmentation.

In an embodiment the module 300, or a further module taking input from module 300, calculates one or more of the indices Sleep time (ST), Total Time at Deep Sleep (DST), Total Time at REM (REMT), Number of Sleep Disruptions (number of awakes during the night after sleep onset) (NSD), Number of SDB events (NSDB).

In an embodiment the indices are combined as:

$$X1*ST+X2*DST+X3*REMT+X4*NSD+X5*NSDB$$

where:

ST score changes linearly [0 for 0 hours, 100 for 7 hours or more]

DST score changes linearly [0 for 0 hours, 100 for 1.5 hours or more]

REMT score changes linearly [0 for 0 hours, 100 for 1.5 hours or more)

NSD score changes linearly [100 for 0, 0 for 10 or more disruptions]

NSDB score changes linearly [100 for 0, 0 for 10 or more events/hour].

Setting X1 to X5 to 0.2, equal weight is given to each score and the resultant sleep score is in the range [0, 1].

Experimental results are described with reference to FIGS. 10-13. Described below is an evaluation of the performance of a system to determine partial sleep staging from the respiratory flow signal alone. In particular, described is the performance of models automatically generated based on flow patterns.

A dataset composed of 50 studies, with full PSG recordings, is used in the experiments. All patients in the study use a modular assisted breathing unit and humidifier system 102 at fixed pressure or pressure auto adjustment mode.

In total, more than 370000 breaths were detected using a breath detector algorithm. To speed up the process of training and testing, half of the samples were used (every second sample). From the remaining 187806 samples, at most 400 samples from each patient were used for training (100 samples from each class), resulting in a training pool of 19607 breaths. The number of training samples is lower than 50×400=20000 because 100 samples of each class were not available in all patients. The test pool was composed of the 168199 samples.

Five-folds cross-validation technique was used for error estimation, where the folds were stratified by patient, i.e., each fold is composed of samples from 10 patients.

During the training procedure, a cost learning matrix was used to give different costs for each error as:

|  | Awake | Light Sleep | Deep Sleep | REM |
|---|---|---|---|---|
| Awake | 0 | 5 | 5 | 10 |
| Light Sleep | 5 | 0 | 5 | 5 |
| Deep Sleep | 5 | 5 | 0 | 5 |
| REM | 10 | 5 | 5 | 0 |

The use of the cost learning matrix aims at reducing errors between specific classes. The aim is to direct the learning procedure to penalise the misclassification between Awake and REM.

Once the training is done and the model is inferred, the operating point is chosen targeting equal TP Rate for all classes. The results of the cross-validated test sets have been used to find the equal TP Rate operating points. Having equal TP Rate in all classes implies that similar numbers of samples are allocated to each class when compared to the results of the mapping module 312.

The best result was obtained with the Random Forest algorithm. In the algorithm 100 decision trees were created and the final classification obtained by combining the results of each tree. The following table shows the resultant confusion matrix. The overall Accuracy was 0.559.

| Confusion matrix | | | | | TP Rate | Precision |
|---|---|---|---|---|---|---|
| 3227 | 2192 | 288 | 172 | Awake | 0.549 | 0.599 |
| 1749 | 13620 | 6170 | 2288 | Light Sleep | 0.571 | 0.643 |
| 223 | 3381 | 4707 | 657 | Deep Sleep | 0.524 | 0.402 |
| 188 | 1964 | 541 | 3574 | REM | 0.570 | 0.534 |

Figure 10:
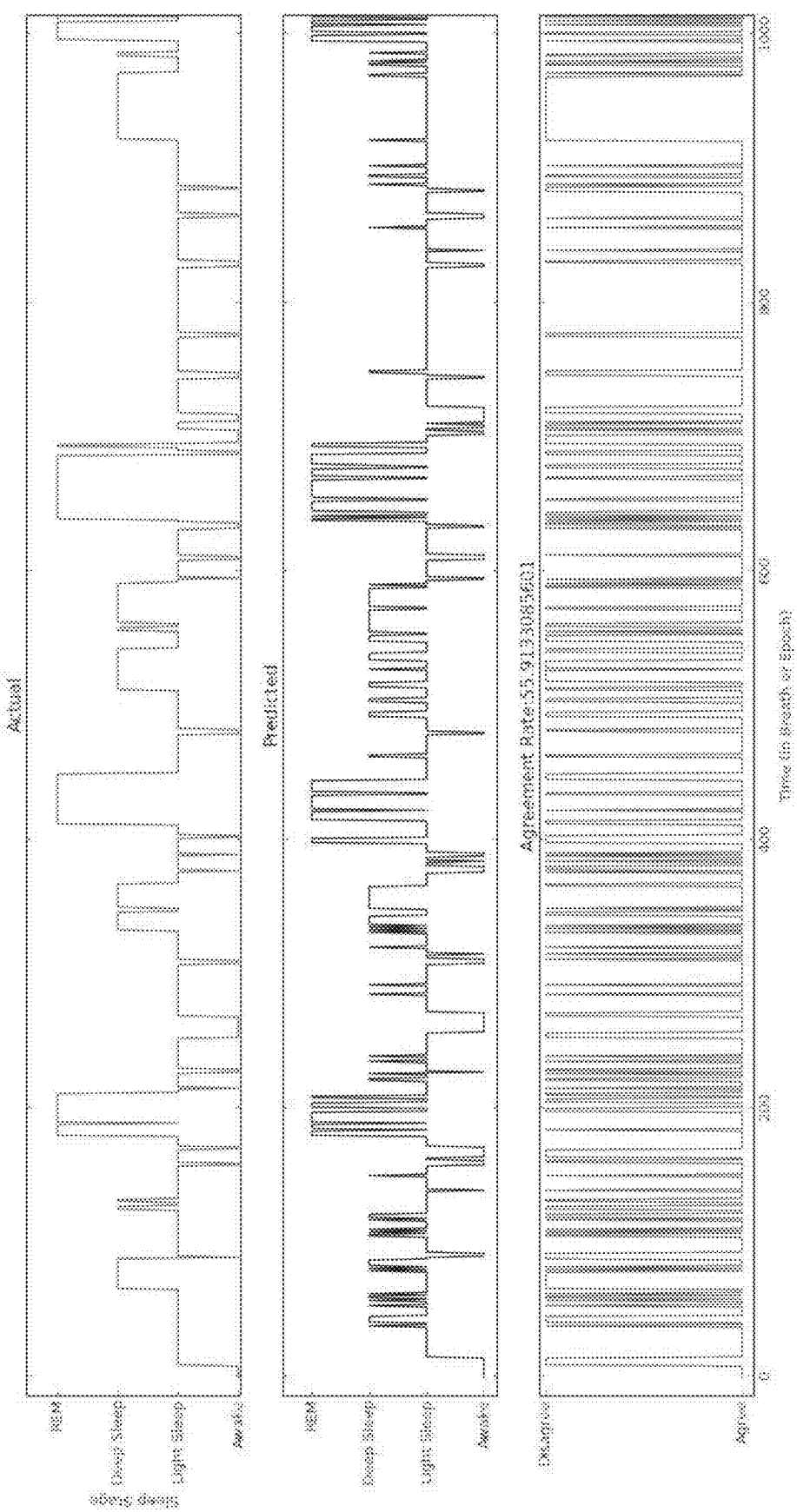
FIG. 10 shows an example of agreement between the mapping module of FIG. 3 and the inferred sleep stages of a test study.

FIG. 10 shows an example of agreement between the mapping module 312 and the inferred sleep stages on a test study.

Figure 11:
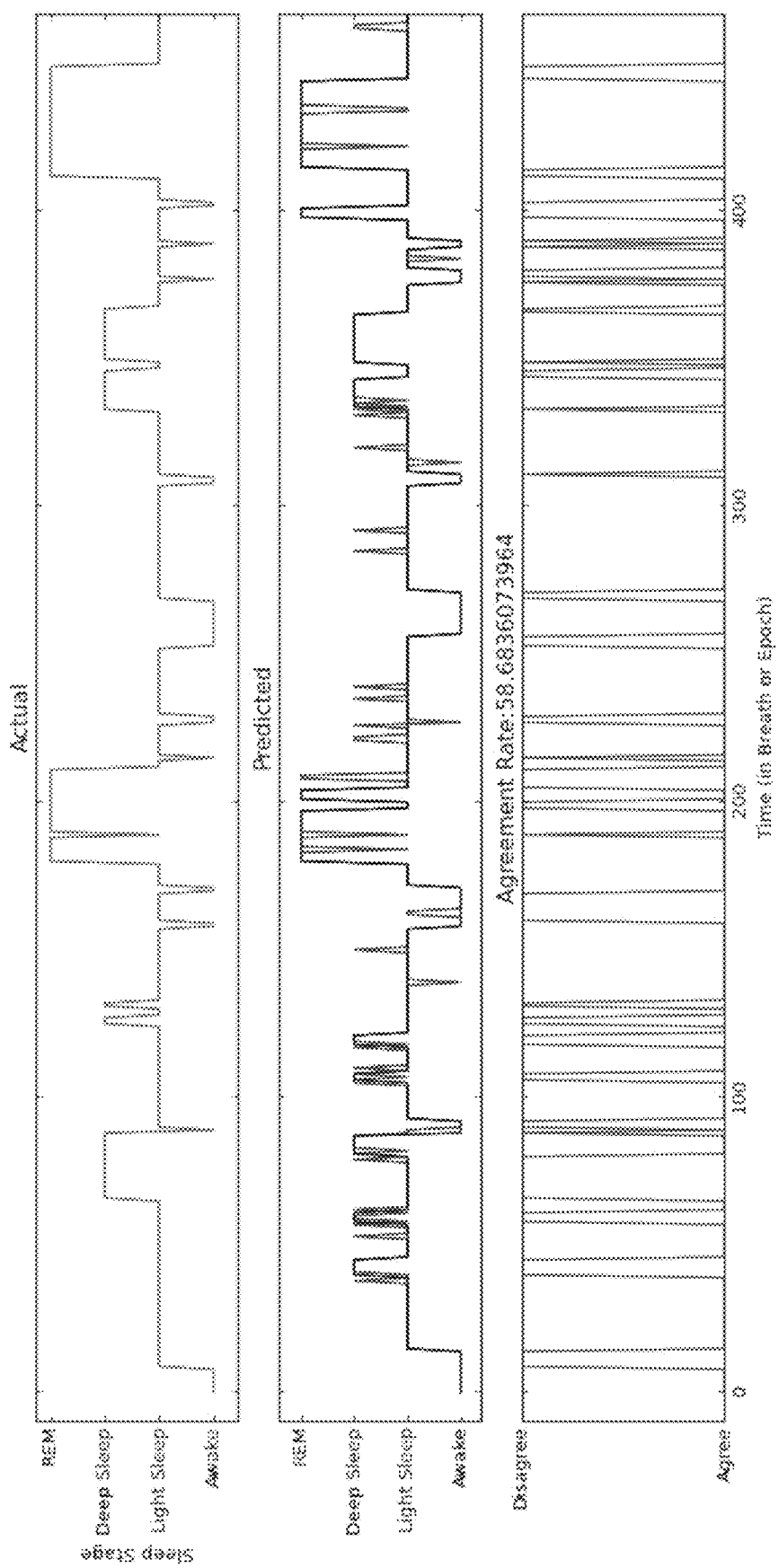
FIG. 11 shows an example function of the context module from FIG. 3 applying contextual clues in an attempt to improve accuracy of the performance of the mapping module.

FIG. 11 shows an application of the context module 314 to improve the accuracy of the mapping module 312.

It can be assumed that individual epochs with differing labels compared to their neighbouring epochs are wrongly detected. This aims at removing states that are likely to have been wrongly detected, by analysing the context where they are placed.

Using majority voting over neighbouring windows, for example recursively until no more changes occur, has the potential to replace extremely short-term stages with neighbouring labels. The number of neighbouring epochs N used for majority voting was set to 7.

By using contextual cues the resultant accuracy increases to 0.602, shown as the confusion matrix in the following table.

| Confusion matrix | | | | | TP Rate | Precision | F-measure |
|---|---|---|---|---|---|---|---|
| 3135 | 2383 | 197 | 124 | Awake | 0.537 | 0.663 | 0.593 |
| 1245 | 15180 | 5847 | 1548 | Light Sleep | 0.637 | 0.658 | 0.648 |
| 207 | 3434 | 4968 | 359 | Deep Sleep | 0.554 | 0.437 | 0.489 |
| 145 | 2067 | 321 | 3731 | REM | 0.596 | 0.648 | 0.620 |

Figure 12:
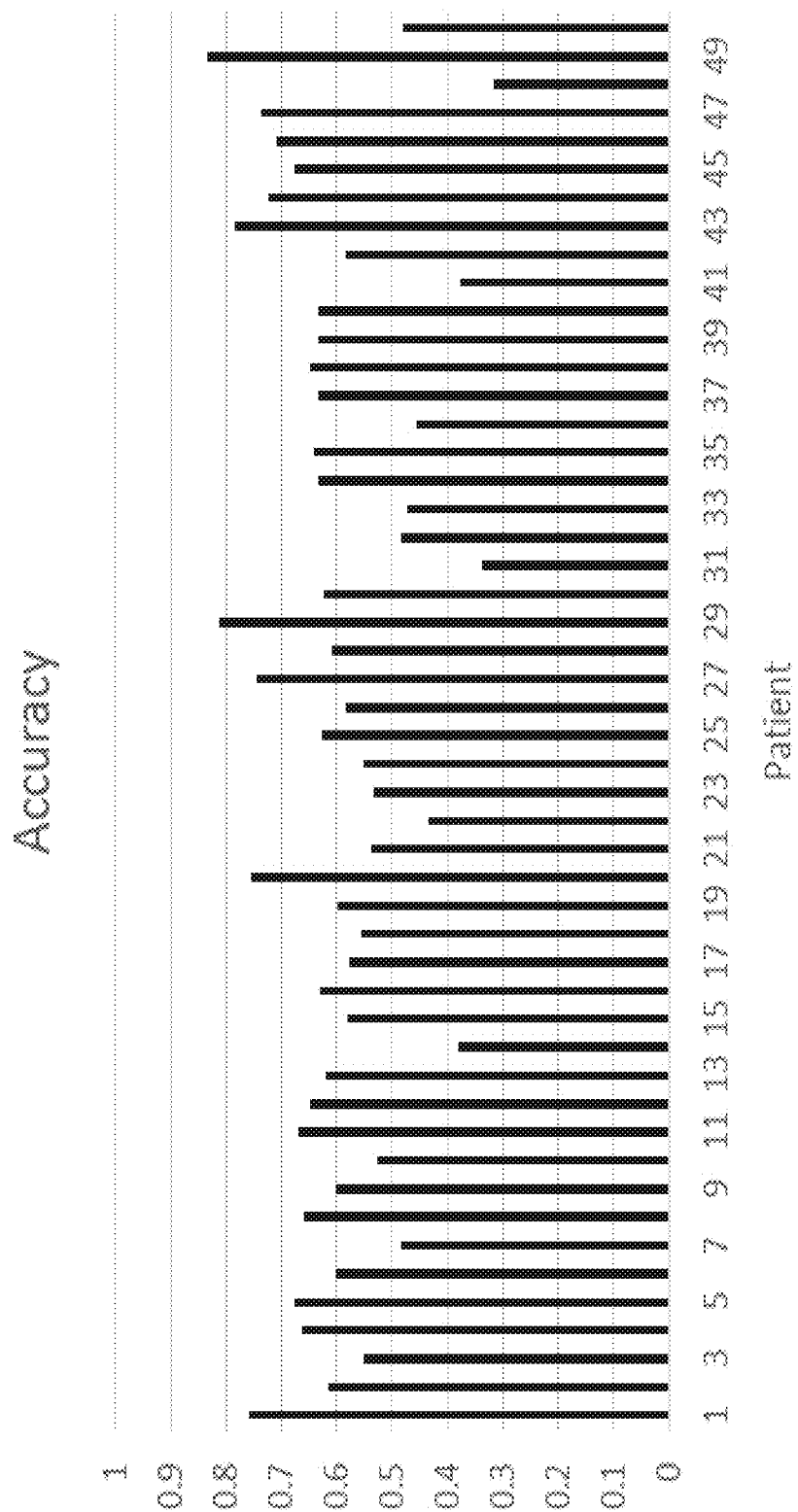
FIG. 12 shows the accuracy per patient of a test study.

FIG. 12 shows the accuracy per patient as having a range varying between [0.31, 0.83], mean=0.6 with 95% confidence that the mean is between [0.57, 0.63].

Figure 13:
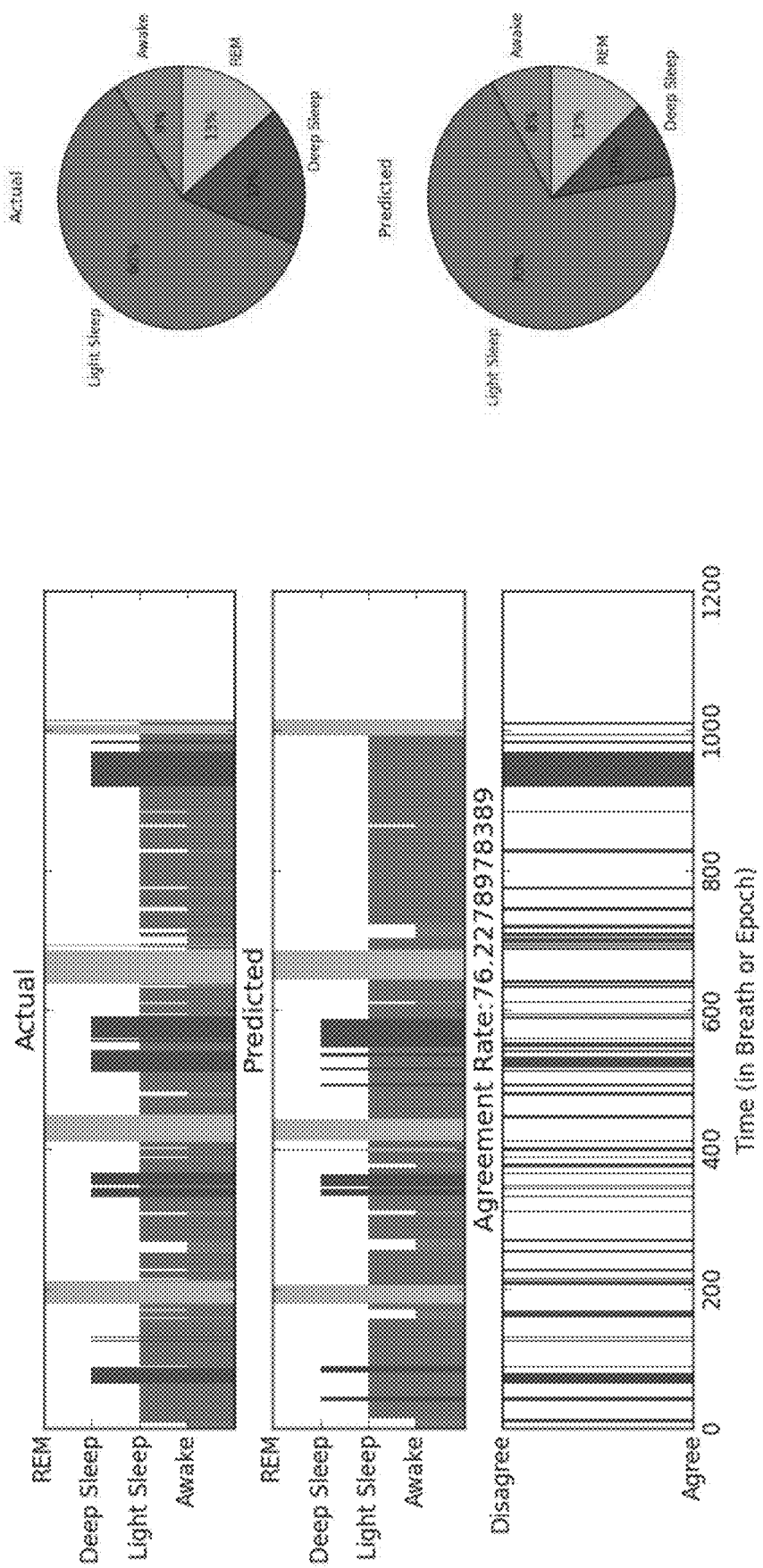
FIG. 13 shows an example of typical performance for an individual patient.

FIG. 13 shows an example of typical performance for an individual patient with agreement of 61.4%.

FIG. 14 shows an example of a system representative of a computing system and/or device that implements module 300 from FIG. 3. The computing device 1400 comprises one or more of a server of a service provider, a device associated with the client (for example a client device), an on-chip system, any other suitable computing device or computing system.

In an embodiment, computing device 1400 includes a processing system 1402, one or more computer-readable media 1404, and one or more Input/Output (I/O) Interfaces 1406 that are communicatively coupled, one to another. In an embodiment the computing device 1400 further includes a system bus or other data and command transfer system (not shown) that couples the various components, one to another. A system bus includes one or more of a memory bus or memory controller, a peripheral bus, a universal serial bus, a processor or local bus that utilizes any of a variety of bus architectures.

The processing system 1402 is representative of functionality to perform one or more operations using hardware. Accordingly, the processing system 1402 is illustrated as including hardware element(s) 1408 configured as one or more of processors and/or functional blocks. This may include implementation in hardware as an application specific integrated circuit or other logic device formed using one or more semiconductors. The hardware elements 1408 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically-executable instructions The computer-readable media 1404 is illustrated as including memory/storage 1410. The memory/storage 1410 represents memory/storage capacity associated with one or more computer-readable media. In an embodiment the memory/storage 1410 includes one or more of volatile media (such as random access memory (RAM)), nonvolatile media (such as read only memory (ROM), Flash memory, optical disks, magnetic disks.

In an embodiment the memory/storage 1410 includes one or more of fixed media (e.g., RAM, ROM, a fixed hard drive), removable media (e.g., Flash memory, a removable hard drive, an optical disc).

Input/output interface(s) 1406 are representative of functionality to allow a user to enter commands and information to computing device 1400, and also allow information to be presented to the user and/or other components or devices using various input/output devices. Examples of input devices include a keyboard, a cursor control device (e.g., a mouse), a microphone (e.g., for voice recognition and/or spoken input), a scanner, touch functionality (e.g., capacitive or other sensors that are configured to detect physical touch), a camera (e.g., which may employ visible or non-visible wavelengths such as infrared frequencies to detect movement that does not involve touch as gestures), and so forth.

Examples of output devices include a display device (e.g., a monitor or projector), speakers, a printer, a network card, tactile-response device, and so forth.

Various techniques are described herein in the general context of software, hardware elements, or program modules. Generally, such modules include routines, programs, objects, elements, components, data structures, and so forth that perform particular tasks or implement particular abstract data types. The terms 'module', 'functionality', and 'component' as used herein generally represent software, firmware, hardware, or a combination thereof. The features of the techniques described herein are platform-independent, meaning that the techniques may be implemented on a variety of commercial computing platforms having a variety of processors.

In an embodiment, an implementation of the described modules and techniques is stored on or transmitted across some form of computer-readable media. The computer-readable media includes a variety of media that may be accessed by the computing device 1400.

Hardware elements 1408 and computer-readable media 1404 are representative of instructions, modules, programmable device logic and/or fixed device logic implemented in a hardware form that may be employed in some embodiments to implement at least some aspects of the techniques described herein.

In an embodiment, hardware elements include one or more of components of an integrated circuit or on-chip system, an application-specific integrated circuit (ASIC), a field-programmable gate array (FPGA), a complex programmable logic device (CPLD). In an embodiment, a hardware element operates as a processing device that performs program tasks defined by instructions, modules, and/or logic embodied by the hardware element as well as a hardware device utilized to store instructions for execution, for example computer-readable storage media.

In an embodiment, software, hardware, or program modules and other program modules are implemented as one or more instructions and/or logic embodied on some form of computer-readable storage media and/or by one or more hardware elements 1408. The computing device 1400 is configured to implement particular instructions and/or functions corresponding to the software and/or hardware modules. Accordingly, implementation of modules that are executable by the computing device 1400 as software may be achieved at least partially in hardware, e.g., through use of computer-readable storage media and/or hardware elements 1408 of the processing system.

In an embodiment the instructions and/or functions are executable/operable by one or more computing devices 1400 and/or processing systems 1402 to implement techniques, modules, and examples described herein.

In an embodiment the computing device 1400 comprises a device selected from a computer class of devices that includes personal computers, desktop computers, multi-screen computers, laptop computers, netbooks. In an embodiment the computing device 1400 comprises a device selected from a mobile class of devices that includes mobile phones, tablet computers, multi-screen computers, wearable devices.

In an embodiment the module 300 and related components is implemented at least partly through use of a distributed system over a cloud 1412 via a platform 1414 for resources 1416. The platform 1414 abstracts underlying functionality of hardware, for example servers, and software resources of the cloud 1412.

In an embodiment the resources 1416 include applications and/or data that are used while computer processing is executed on servers that are remote from the computing device 1400. In an embodiment, resources 1416 include services provided over the Internet and/or through a subscriber network, such as a cellular or Wi-Fi network.

In an embodiment, platform 1414 abstracts resources and functions to connect the computing device 1400 with other computing devices. In an embodiment the platform 1414 serves to abstract scaling of resources to provide a corresponding level of scale to encountered demand for the resources 1416 that are implemented via the platform 1414.

In an interconnected device embodiment, implementation of functionality described herein tends to be distributed. For example, in an embodiment, the functionality is implemented in part on the computing device 1400 as well as via the platform 1414 that abstracts the functionality of the cloud 1412.

The foregoing description of the invention includes preferred forms thereof. Modifications may be made thereto without departing from the scope of the invention, as defined by the accompanying claims.

The invention claimed is:

1. A method of automatically determining a sleep stage of a user using a respiratory system configured to provide respiratory therapy to the user, the method comprising:
    using a controller of the respiratory system and one or more sensors of the respiratory system:
        receiving a respiratory flow signal of the user from the one or more sensors;
        obtaining at least one centre of mass measurement from the respiratory flow signal;
        automatically determining the sleep stage of the user from the at least one centre of mass measurement; and
        using the determined sleep stage of the user to adjust an operational parameter of the respiratory therapy.

2. The method of claim 1 further comprising obtaining at least one duration measurement from the respiratory flow signal, wherein automatically determining the sleep stage of the user further comprises automatically determining the sleep stage of the user from the at least one duration measurement.

3. The method of claim 2 wherein the at least one duration measurement includes one or more of breath duration, inspiration duration, maximum inspiration time, maximum expiration time, a function of maximum expiration time and maximum inspiration time, or a function of inspiration duration and breath duration.

4. The method of claim 1 further comprising obtaining at least one amplitude measurement from the respiratory flow signal, wherein automatically determining the sleep stage of the user further comprises automatically determining the sleep stage of the user from the at least one amplitude measurement.

5. The method of claim 4 wherein the at least one amplitude measurement includes one or more of maximum inspiration amplitude, maximum expiration amplitude, or a function of maximum inspiration amplitude and maximum expiration amplitude.

6. The method of claim 1 wherein the at least one centre of mass measurement includes one or both of:
    a function with variables including expiration centre of mass time and inspiration centre of mass time; or a function with variables including expiration centre of mass amplitude and inspiration centre of mass amplitude.

7. The method of claim 1 further comprising obtaining at least one derivative related measurement from the respiratory flow signal, wherein automatically determining the sleep stage of the user further comprises automatically determining the sleep stage of the user from the at least one derivative related measurement.

8. The method of claim 7 wherein the at least one derivative related measurement includes one or more of maximum negative acceleration time, maximum negative acceleration amplitude, maximum positive acceleration time, maximum positive acceleration amplitude, maximum negative flow rate time, maximum negative flow rate amplitude, maximum inspiration acceleration time, or maximum inspiration acceleration amplitude.

9. The method of claim 1 further comprising obtaining at least one volume related measurement from the respiratory flow signal, wherein automatically determining the sleep stage of the user further comprises automatically determining the sleep stage of the user from the at least one volume related measurement.

10. The method of claim 9 wherein the at least one volume related measurement includes one or more of inspiration volume, expiration volume, or a function of inspiration volume and expiration volume.

11. The method of claim 1 further comprising:
identifying, within the respiratory flow signal, at least one breath signal representing a breath of the user; and
obtaining at least one breath measurement from a portion of the respiratory flow signal within which the at least one breath signal is identified.

12. The method of claim 11 further comprising:
identifying, within the respiratory flow signal, a window containing a plurality of breath signals; and
obtaining respective breath measurements of the breath signals within the window.

13. The method of claim 12 wherein automatically determining the sleep stage of the user further comprises automatically determining the sleep stage of the user from at least one of a mean or a standard deviation of the breath measurements within at least part of the window.

14. The method of claim 1 further comprising determining the sleep stage from the at least one centre of mass measurement at least partly by applying at least one of a supervised learning algorithm, an unsupervised learning algorithm, or a semi-supervised learning algorithm.

15. The method of claim 1 wherein the sleep stage is one of a plurality of sleep stages configured to be determined by the method, the plurality of sleep stages comprising:
awake, N1, N2, N3, and REM;
awake, light sleep, deep sleep, and REM;
awake, non-REM, and REM; or
awake and asleep.

16. The method of claim 1 wherein the at least one centre of mass measurement includes:
one or both of inspiration centre of mass time or mass amplitude; and
one or both of expiration centre of mass time or mass amplitude.

17. The method of claim 1 wherein using the determined sleep stage of the user to adjust an operational parameter of the respiratory therapy comprises outputting control signals to adjust power to an air supply of the respiratory system based at least in part on the automatically determined sleep stage of the user.

18. A respiratory system configured to provide respiratory therapy to a user and automatically determine a sleep stage of the user, the system comprising:
a controller in electrical communication with one or more sensors located at the respiratory system and configured to receive a respiratory flow signal of the user from the one or more sensors, the controller comprising:
a feature extractor configured to obtain at least one centre of mass measurement from at least part of the respiratory flow signal of the user; and
a mapping module configured to automatically determine the sleep stage of the user from the at least one centre of mass measurement,
wherein the controller is further configured to use the determined sleep stage of the user to adjust an operational parameter of the respiratory therapy.

19. A respiratory system configured to provide respiratory therapy to a user and automatically determine a sleep stage of the user, the system comprising:
a processor in electrical communication with one or more sensors located at the respiratory system; and
a computer readable medium having stored thereon computer executable instructions that, when executed by the processor, cause the processor to perform a method of determining the sleep stage of the user, the method comprising:
receiving a respiratory flow signal of the user from the one or more sensors;
obtaining at least one centre of mass measurement from at least part of the respiratory flow signal;
automatically determining the sleep stage of the user from the at least one centre of mass measurement; and
using the determined sleep stage of the user to adjust an operational parameter of the respiratory therapy.

20. A computer readable medium of a respiratory system configured to provide respiratory therapy to a user, the medium having stored thereon computer-executable instructions that, when executed by a processor of the respiratory system that is in electrical communication with one or more sensors located at the respiratory system, cause the processor to perform a method of automatically determining a sleep stage of a user, the method comprising:
receiving a respiratory flow signal of the user from the one or more sensors;
obtaining at least one centre of mass measurement from at least part of the respiratory flow signal;
automatically determining the sleep stage of the user from the at least one centre of mass measurement; and
using the determined sleep stage of the user to adjust an operational parameter of the respiratory therapy.

* * * * *